US010021901B2

(12) United States Patent
Pimentel et al.

(10) Patent No.: US 10,021,901 B2
(45) **Date of Patent: *Jul. 17, 2018**

(54) ANTIMICROBIAL MIXTURE OF ALDEHYDES, ORGANIC ACIDS AND FATTY ACID ESTERS

(71) Applicant: ANITOX CORPORATION, Lawrenceville, GA (US)

(72) Inventors: Julio Pimentel, Buford, GA (US); Kurt Richardson, Maysville, GA (US)

(73) Assignee: ANITOX CORPORATION, Lawrenceville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,428

(22) PCT Filed: Nov. 6, 2012

(86) PCT No.: PCT/US2012/063655

§ 371 (c)(1), (2) Date: May 15, 2014

(87) PCT Pub. No.: WO2013/081777

PCT Pub. Date: Jun. 6, 2013

(65) Prior Publication Data

US 2014/0323572 A1 Oct. 30, 2014

Related U.S. Application Data

(60) Provisional application No. 61/565,276, filed on Nov. 30, 2011.

(51) Int. Cl.

| | |
|---|---|
| ***A23L 3/3499*** | (2006.01) |
| ***A23L 3/3517*** | (2006.01) |
| ***A23L 3/3508*** | (2006.01) |
| ***A01N 35/02*** | (2006.01) |
| ***A01N 37/02*** | (2006.01) |
| ***A23L 3/3463*** | (2006.01) |
| ***C02F 1/50*** | (2006.01) |

(52) U.S. Cl.

CPC .......... *A23L 3/34635* (2013.01); *A01N 35/02* (2013.01); *A01N 37/02* (2013.01); *A23L 3/3508* (2013.01); *A23L 3/3517* (2013.01); *C02F 1/50* (2013.01)

(58) Field of Classification Search

CPC .... A23L 3/3499; A23L 3/3508; A23L 3/3517; A01N 37/02; A01N 35/02

See application file for complete search history.

(56) References Cited

U.S. PATENT DOCUMENTS

| | | | |
|---|---|---|---|
| 3,615,653 | A | 10/1971 | Fults et al. |
| 3,682,653 | A | 8/1972 | Mommer |
| 4,701,331 | A | 10/1987 | Grabitz |
| 4,772,481 | A | 9/1988 | Rohwer et al. |
| 4,824,686 | A | 4/1989 | Dunn et al. |
| 5,093,124 | A | 3/1992 | Kulenkampff |
| 5,139,779 | A | 8/1992 | McNeff |
| 5,198,253 | A | 3/1993 | Roskowiak et al. |
| 5,240,727 | A | 8/1993 | McNeff |
| 5,260,260 | A | 11/1993 | Gednalske et al. |
| 5,279,838 | A | 1/1994 | McNeff |
| 5,342,630 | A | 8/1994 | Jones |
| 5,366,995 | A | 11/1994 | Savage et al. |
| 5,505,976 | A | 4/1996 | Bland et al. |
| 5,518,750 | A | 5/1996 | Mcneff |
| 5,547,987 | A | 8/1996 | Bland et al. |
| 5,587,358 | A | 12/1996 | Sukigara et al. |
| 5,591,467 | A | 1/1997 | Bland et al. |
| 5,663,152 | A | 9/1997 | Hayano et al. |
| 5,698,599 | A | 12/1997 | Subbiah |
| 5,776,919 | A | 7/1998 | Sukigara et al. |
| 5,911,915 | A | 6/1999 | Fonsny et al. |
| 6,103,768 | A | 8/2000 | Savage et al. |
| 6,121,224 | A | 9/2000 | Fonsny et al. |
| 6,136,856 | A | 10/2000 | Savage et al. |
| 6,201,026 | B1 | 3/2001 | Hammond et al. |
| 6,218,336 | B1 | 4/2001 | Coleman |
| 6,221,381 | B1 | 4/2001 | Shelford et al. |
| 6,323,171 | B1 | 11/2001 | Fonsny et al. |
| 6,326,032 | B1 | 12/2001 | Richter et al. |
| 6,468,953 | B1 | 10/2002 | Hitchems et al. |
| 6,387,866 | B1 | 11/2002 | Mondin et al. |

(Continued)

FOREIGN PATENT DOCUMENTS

| | | | |
|---|---|---|---|
| AU | 1631795 | A | 11/1995 |
| CN | 101233852 | A | 8/2008 |

(Continued)

OTHER PUBLICATIONS

Burdock, in Fenaroli's Handbook of Flavor Ingredients, 5th Edition, CRC Press, Boca Raton, 2005, p. 1330.*
Yeager, D., 2010. Food Safety Update—Report Underscores Need for Enhanced l.eg;slation to Protect ,4mericans Today's Dietitian 12(6): 42.
ESR EP 12854061.4.
Ona Nivinskiene et al: "Influence of urban environment on chemical composition of Tilia cordata essential oil", Chemija, vol. 18, No. 1, pp. 44-49, 2007.
Afifa Bergaoui et al: "Chemical Composition and Antifungal Activity of Volatiles from Three Opuntia Species Growing in Tunisia", Pakistan Journal of Biological Sciences, vol. 10, No. 15, (Jan. 1, 2007), pp. 2485-2489.
Nandi et al: "Volatile aldehydes, ketones, esters and terpenoids as preservatives against storage fungi in wheat", Journal of Plant Diseases and Protection, vol. 83, No. 5, (Jan. 1, 1976), pp. 284-294.
International Search Report for PCT/US2012/063655.

(Continued)

*Primary Examiner* — Irina Neagu
(74) *Attorney, Agent, or Firm* — Thompson Coburn LLP; Steven M. Ritchey

(57) ABSTRACT

An antimicrobial composition and method for extending the shelf-life of water, food/feed or food/feed ingredients, comprising: 5-25 wt. % nonanoic acid, 1-25 wt. % organic acid ester, 1-50 wt. % of a single or mixture of $C_1$-$C_{24}$ aldehydes, a mixture of $C_1$-$C_{24}$ organic acids, and water.

4 Claims, No Drawings

(56) References Cited

U.S. PATENT DOCUMENTS

| | | | | |
|---|---|---|---|---|
| 6,479,044 | B1 | 11/2002 | Mahieu et al. | |
| 6,479,454 | B1 | 11/2002 | Smith et al. | |
| 6,482,463 | B1 | 11/2002 | Mologni et al. | |
| 6,596,681 | B1 | 7/2003 | Mahieu et al. | |
| 6,596,763 | B1 | 7/2003 | Thormar et al. | |
| 6,638,978 | B1 | 10/2003 | Kabara | |
| 6,960,350 | B2 | 11/2005 | Hanada et al. | |
| 7,134,957 | B2 | 11/2006 | Clayton et al. | |
| 7,638,114 | B1 | 12/2009 | Schur | |
| 7,645,464 | B2 | 1/2010 | Hansen | |
| 7,652,067 | B2 | 1/2010 | Erman et al. | |
| RE41,279 | E | 4/2010 | McSherry et al. | |
| 7,862,842 | B2 | 1/2011 | Beltran et al. | |
| 2001/0046979 | A1* | 11/2001 | Roselle et al. | 514/160 |
| 2002/0009527 | A1 | 1/2002 | Bland et al. | |
| 2002/0034568 | A1 | 3/2002 | Blyth et al. | |
| 2003/0176500 | A1* | 9/2003 | Molly et al. | 514/547 |
| 2003/0228402 | A1 | 12/2003 | Franklin et al. | |
| 2004/0266852 | A1 | 12/2004 | Coleman | |
| 2005/0031744 | A1 | 2/2005 | Paliyath | |
| 2005/0161636 | A1 | 7/2005 | Man et al. | |
| 2005/0170052 | A1 | 8/2005 | Pimentel | |
| 2005/0192197 | A1 | 9/2005 | Man et al. | |
| 2005/0214291 | A1 | 9/2005 | Lee et al. | |
| 2005/0260243 | A1 | 11/2005 | Lynch et al. | |
| 2007/0027119 | A1 | 2/2007 | Ahmed et al. | |
| 2007/0087094 | A1 | 4/2007 | Schuer | |
| 2009/0061017 | A1 | 3/2009 | Pedersen et al. | |
| 2009/0082253 | A1 | 3/2009 | Otto et al. | |
| 2009/0263549 | A1 | 10/2009 | Kleve et al. | |
| 2010/0204323 | A1 | 8/2010 | Theiler et al. | |
| 2010/0234460 | A1 | 9/2010 | Foret et al. | |
| 2012/0252893 | A1 | 4/2012 | Pimentel | |
| 2012/0128843 | A1* | 5/2012 | Richardson et al. | 426/335 |
| 2015/0031762 | A1* | 1/2015 | Pimentel et al. | 514/557 |
| 2015/0208697 | A1 | 7/2015 | Richardson et al. | |

FOREIGN PATENT DOCUMENTS

| | | | |
|---|---|---|---|
| CN | 102469810 | | 5/2012 |
| DE | 161 131 | A1 | 2/1985 |
| EP | 0208403 | A1 | 1/1987 |
| EP | 0244144 | A1 | 11/1987 |
| EP | 0363733 | A2 | 4/1990 |
| EP | 2283733 | A1 | 2/2011 |
| JP | 1987126938 | A | 6/1987 |
| JP | 2000-325037 | | 11/2000 |
| JP | 2003535894 | A | 12/2003 |
| JP | 2005511635 | A | 4/2005 |
| JP | 2007505125 | A | 3/2007 |
| JP | 5655075 | B2 | 1/2015 |
| RU | 99101491 | A | 11/2000 |
| RU | 2176889 | C2 | 12/2001 |
| RU | 2288592 | C1 | 12/2006 |
| RU | 2303357 | C2 | 7/2007 |
| RU | 2321273 | C1 | 4/2008 |
| SU | 701631 | A1 | 12/1979 |
| WO | 95/28091 | A1 | 10/1995 |
| WO | 96/11585 | A1 | 4/1996 |
| WO | 96/24247 | A1 | 8/1996 |
| WO | 97/28896 | A1 | 8/1997 |
| WO | 97/42836 | A1 | 11/1997 |
| WO | 98/03066 | A1 | 1/1998 |
| WO | 99/37172 | A1 | 7/1999 |
| WO | 99/60865 | A1 | 12/1999 |
| WO | 01/32020 | A2 | 5/2001 |
| WO | WO 01/97799 | | 12/2001 |
| WO | 02/38684 | A1 | 5/2002 |
| WO | 03/044145 | A1 | 5/2003 |
| WO | WO 03/070181 | | 8/2003 |
| WO | 03/096807 | A1 | 11/2003 |
| WO | 2006/024620 | A1 | 3/2006 |
| WO | 2008/031087 | A1 | 3/2008 |
| WO | WO 2009/037270 | | 3/2009 |
| WO | WO 2011/017367 | | 2/2011 |
| WO | WO 2011/025496 | | 3/2011 |

OTHER PUBLICATIONS

Written Opinion of the International Search Authority for PCT/US2012/063655.

Search Report in related Taiwanese Application No. 101147408.

Andersen, R. A.; Hamilton-Kemp, T.; Hilderbrand, D. F.; McCraken Jr., C. T.; Collins, R. W.; Fleming, P. D. Structure-Antifungal Activity Relationships among Volatile C6 and C9 Aliphatic Aldehydes, Ketones, and Alcohols. J. Agric. Food Chern. 1994, v. 42, 1563-1568.

Aneja, M., T. J . Gianfagna,and K. P. Hebbar, 2005. 7richoderma harzianumproduces nonanoic acid, an inhibitor of spore germination and mycelial growth of two cacao pathogens. Physiol. Mol. Plant Pathol. 67: 304-307.

Archbold, D., T. Hamilton-Kemp, A. Clements, and R. Collins, 1994. Fumigating 'Crimson Seedless' Table Grapes with (E}-2-Hexenal Reduces Mold during Long-term Postharvest Storage. HortScience 34(4): 705-707.

Babic, I., S. Aubert,M.J. Amiot and C. Nguyen-The, 1994. Antimicrobial Activity of Shredded Carrot Extracts on Food-borne Bacteria and Yeast. J. Applied Bacteriology 76(2): 135-141.

Beck, J.J., S.c. Chou, B.C. Campbell and J.H. Kim, 2007. Fungicidal Activities of Dihydroferulic Acid Alkyl Ester Analogues. J. Natural Products 70(5): 779-782.

Belletti, N.,S. Kamdem, F. Patrignani,R. Lanciotti, A. Covelli,and F. Gardini, 2007. Antimicrobial Activity of Aroma Compounds against *Saccharomyces cerevisiae* and Improvement of Microbiological Stability of Soft Drinks as Assessed by Logistic Regression. AEM. 73 (17): 5580-5586.

Bisignano, G., M. G. Lagana, D. Trombetta "S. Arena" A. Nostro,N. Uccella, G. Mazzanti,and A. Saija, 2001. In vitro antibacterial activity of some aliphatic aldehydes from Olea europaea L. FEMS Microbiology Letters 198: 9-13.

Chadeganipour and Haims, 2001 Antifungal activities of nonanoic and capric acid on Microsporum gypseum. Mycoses 44(3-4): 109-112.

Chandrasekaran, M., A. Senthilkumar and V. Venkatesalu, 2011. Antibacterial and Antifungal Efficacy of Organic Acid Methyl Esters from the Leaves of *Sesuvium portulacastrum* L. Eur.Rev. Med. & Pharmacol. Sci. 15 (7): 775-780.

Choi G.J., K.S. Jang, V.H. Choi, J.H. Vu, and J.c. Kim, 2010. Antifungal Activity of Lower Alkyl Organic Acid Esters Against Powdery Mildews. The Plant Pathology Journal 26(4): 360.

Deng, W., T. Hamilton-Kemp, M. Nielsen, R. Anderson, G. Collins, and D.; Hilderbrand 1993. Effects of Six-Carbon Aldehydes and Alcohols on Bacterial Proliferation. J. Agric. Food Chem. 41: 506-510.

Fallik, E., D.O. Archbold, T.R. Hamilton-Kemp,A.M. Clements, R.W. Collins, and M.M. Barth.1998. {E)-2-hexenal can stimulate Botrytis cinerea growth in vitro and on strawberries invivo during storage. J. Amer. Soc. Hort. Sci.123:875-881.

Gardini, F.; Lanciotti, R.; Guerzoni, M.E., 2001. Effect of trans-2-hexenal on the growth of Aspergillus flavus in relation to its concentration, temperature and water activity. Letters in App. Microbiology 33: 50-55.

Hamilton-Kemp T.R., lH. Loughrin, D.O. Archbold, R.A. Andersen and D.F. Hildebrand, 1991. Inhibition of pollen germination by volatilecompounds including 2-hexenal and 3-hexenal. J Agric. Food Chem 39: 952-956.

Hirazawa, N., 2001. Antiparasitic effect of medium-chain organic acids against ciliated Cryptocaryon irritans infestation in the red sea bream *Pagrus major*. Aquaculture 198: 219-228.

Huang, C.B., B. George and J.L. Ebersole, 2010. Antimicrobial Activity of n-6, n-7 and n-9 Organic Acids and Their Esters for Oral Microorganisms. Arch. Oral Biology 55(8): 555-560.

Hubert, J., Z. Munzbergova and A. Santino, 2008. Plant volatile aldehydes as natural insecticides against stored-product beetles. Pest Manag. Sci. 64: 57-64.

(56) References Cited

OTHER PUBLICATIONS

Kim, Y. S. and D.H. Shin, D. H., 2004. Volatile Constituents from the Leaves of Callicarpa japonica Thunb. and Their Antibacterial Activities. 1 Agric. Food Chem. 52: 781-787.
Kubo, l, 1 R. Lee, and I. Kubo, 1999. Anti-Helicobacter pylori Agents from the Cashew Apple. 1 Agric. Food Chem. 47: 533-537.
Kubo, I. and K. Fujita,2001. Naturally Occurring Anti-*Salmonella* Agents. 1 Agric. Food Chem. 49: 5750-5754.
Lederer, B., T. Fujimori, Y. Tsujino, K. Wakabayashi and P. Boger, 2004. Phytotoxic activity of middle-chain organic acids II: peroxidation and membrane effects. Pesticide Biochemistry and Physiology 80: 151-156.
Madriz-Guzman, A., I. Martinez and M. Guzman, 2008. In vitro Effect and in the Field of Methyl Esters oils from Castor, Palm and Soybean on Mycosphaerella /ijiensis, Causal Agent of Black Sigatoka in Bananas (Musa AAA). Corbana. 34 (61): 11-27 San Jose: Corporacion bananera Nacional.
Merkl, R., I. Hradkova, V. Filip and J. Smidrkal, 2010. Antimicrobial and Antioxidant Properties of Phenolic Acids Alkyl Esters. Czech J. Food Sci. 28(4): 275-279.
Muroi, H., A. Kubo, and I. Kubo, 1993. Antimicrobial Activity of Cashew Apple Flavor Compounds. J. Agric. Food Chem. 41: 1106-1109.
Nakamura, S. and A. Hatanaka, 2002. Green-leaf-derived C6-aroma compounds with potent antibacterial action that act on both gram-negative and gram-positive bacteria. J. Agric. Food Chem. 50(26): 7639-7644.
Neri, F., M. Mari, S. Brigati, and P. Bertolini, 2007. Fungicidal activity of plant volatile compounds for controlling Mono/inia /axa in stone fruit. Plant Disease 91(1): 30-35.
Neri, F.,M. Mari, A. Menniti, S. Brigati, and P. Bertolini, 2006a. Control of Penicillium expansum in pears and apples by trans-2-hexenal vapors. Postharvest Biol. and Tech. 41: 101-108.
Neri, F.M. Mari, A. M. Menniti, and S. Brigati 2006b. Activity of trans-2-hexenal against Penicillium expansum in 'Conference' pears. J. Appl. Microbiol. 100: 1186-1193.
Paster, N. , 1979. A commercial study of the efficiency of propionic acid and acid and calcium propionate as fungistats in poultry feed, Poult. Sci. 58: 572-576.
Patrignani, F., L. Lucci, N. Belletti, F. Gardini, M. E. Guerzoni, and R. Lanciotti, 2008. Effects of sub-lethal concentrations of hexanal and 2-(E)-hexenal on membrane organic acid composition and volatile compounds of Listeria monocytogenes, *Staphylococcus aureus*, *Salmonella enteritidis* and *Escherichia coli*. International J. Food Micro. 123: 1-8.
Sadek, E.M., A.M. Motawie, A.M. Hassan and E.A. Gad, 1994. Synthesis and Evaluation of Some Organic Esters as Plasticizers and Fungicides. J. Chem. Technology and Biotechnology. 63(2): 160-164.
Saniewska, S. and M. Saniewski, 2007. The effect of trans-2-hexenal and trans-2-nonenal on the mycelium growth of Phoma narcissi in vitro, Rocz. AR. Pozn. CCCLXXXIII, Ogrodn. 41: 189-193.
Strobel, S.A. ,E. Dirkse, J. Sears, and C. Markworth, 2001. Volatile Antimicrobial from *Muscodor albus*, a Novel Endophytic fungus. Microbiology 147: 2943-2950.
Van Immerseel, F., J.B. Russell, M.D. Flythe, I. Gantois, L. Timbermont, F. Pasmans, F. Haesebrouck, and R. Ducatelle, 2006. The use of organic acids to combat *Salmonella* in poultry: a mechanistic explanation of the efficacy. Avian Pathology 35(3): 182-188.
Yeager, D., 2010. Food Safety Update—Report Underscores Need for Enhanced 1.eg;slation to Protect ,4mericans Today's Dietitian 12(6): 42.
Anderson et al., "Effect of Drinking-Water Administration of Experimental Chlorate Ion Preparations on *Salmonella enterica* Serovar Typhimurium Colonization in Weaned and Finished Pigs", Veterinary Research Communications, 2004, pp. 179-189, vol. 28 No. 3.
Henderson et al., "Early Events in the Pathogenesis of Avian Salmonellosis", Infection and Immunity, 1999, pp. 3580-3586, vol. 67 No. 7.
Humphrey et al., "Contamination of Egg Shell and Contents with *Salmonella enteritidis*", International Journal of Food Microbiology, 1994, pp. 31-40, vol. 21 No. 1-2.
International Preliminary Report on Patentability for PCT/US2010/044305 dated Feb. 7, 2012.
International Search Report for PCT/US2010/044305 dated Apr. 20, 2011.
Keller et al., "*Salmonella enteritidis* Colonization of the Reproductive Tract and Forming and Freshly Laid Eggs of Chickens", Infection and Immunity, 1995, pp. 2443-2449, vol. 63 No. 7.
Supplementary European Search Report for EP 10807056 dated Sep. 15, 2014.
Chandler et al., "Characterization of the Wetting and Dewetting Behavior of Powders", KONA Powder and Particle Journal, 2007, pp. 56-75, vol. 25.
Clark et al., "Effects of Marker Selection and Mix Time on the Coefficient of Variation (Mix Uniformity) of Broiler Feed", Journal of Applied Poultry Research, 2007, pp. 464-470, vol. 16.
Cosmetic Ingredient Review, "Final Report on the Safety Assessment of PEG-30, -33, -35, -36, and -40 Castor Oil and PEG-30 and PEG-40 Hydrogenated Castor Oil", International Journal of Toxicology, 1997, pp. 269-306, vol. 16.
Froetschner, Marketing Manager, DSM Nutritional Products, Inc. Parsippany, NJ, "Mixing: A Detailed Look at the Factors that Influence Mix Uniformity" nmfeed.com/files/posts/portal1/4(70).pdf, Penn State Dairy Cattle Nutrition Workshop, 2005, pp. 19-38.
Fruijtier-Polloth, "Safety Assessment on Polyethylene Glycols (PEGs) and their Derivatives as used in Cosmetic Products", Toxicology, 2005, pp. 1-38, vol. 214.
Herrman et al., "Testing Mixer Performance". Kansas State University Extension Service Bulletin, 1994, pp. 1-4.
International Search Report for PCT/US2012/046821 dated Apr. 4, 2013.
Meyer et al., "Determination of Cremophor® EL in Plasma after Sample Preparation with Solid Phase Extraction and Plasma Protein Precipitation", Journal of Pharmaceutical and Biomedical Analysis, 2001, pp. 495-506, vol. 24.
Polkhovskaya N. kompaniya Biochem na konferentsii <<Kombikorma-2012>>, Jun. 6, 2012, [online] [Retrieved on Feb. 26, 2013] Retrieved from the Internet: URL:http://www.milkua.info.uklcompanynews/464/, pp. 1-2.
Singh, "Effect of Different Additives on Cloud Point of Non Iconic Surfactant", Bachelor of Technology thesis, Department of Chemical Engineering, National Institue of Technology, Rourkela, India, 2001.
Stark et al., "On-farm Feed Uniformity Survey", Swine Day Report No. 641 Kansas State University, 1991, pp. 144-145.
Written Opinion of the International Search Authority for PCT/US2012/046821 dated Apr. 4, 2013.
Haque et al., "Propionic Acid is an Alternative to Antibiotics in Poultry Diet", Bangladesh Journal of Animal Science, 2009, pp. 115-122, vol. 38, No. 1&2.
Karabinos et al., "Bactericidal Activity of Certain Fatty Acids", The Journal of American Oil Chemists's Society, Jun. 1954, pp. 228-232, vol. 31.
Lin et al., "Comparative Analysis of Extreme Acid Survival in *Salmonella typhimurium*, Shigella flexneri, and *Esherichia coli*", Journal of Bacteriology, Jul. 1995, pp. 4097-4104, vol. 177, No. 14.
Opdyke, "Fragrance Raw Material Monographs", Food and Cosmetics Toxicology, Jun. 1974, pp. 839-841, vol. 12.
Opposition against EP2768539, filed on Sep. 4, 2017, 16 pages.
Opposition against EP3023009, Filed on Sep. 4, 2017, 15 pages.
Ponce De Leon et al., "Effect of Acetic and Citric Acids on the Growth and Activity (VB-N) of *Pseudomonas* sp. and *Moraxella* sp.", Bulletin of the Faculty of Fisheries Hokkaido University, May 1993, pp. 80-85, vol. 44, No. 2.
Results of Experiments on the Antimicrobial Effects of the Compositions Claimed of Various Microorganisms, Sep. 4, 2017, 1 page.

* cited by examiner

ANTIMICROBIAL MIXTURE OF ALDEHYDES, ORGANIC ACIDS AND FATTY ACID ESTERS

CROSS REFERENCE TO RELATED APPLICATIONS

This application is a national stage entry of PCT/US12/63655, filed Nov. 6, 2012, which published as WO2013/081777 on Jun. 6, 2013, and claims priority to provisional Application No. 61/565,276, filed Nov. 30, 2011, entitled "Antimicrobial Mixture of Aldehydes, Organic Acids and Fatty Acid Esters", which is hereby incorporated by reference.

BACKGROUND OF THE INVENTION

Field of the Invention

An antimicrobial formulation containing a mixture of organic acids, aldehydes and organic acid esters, where such combination results in a synergistic response.

Background

The Centers for Disease Control and Prevention (CDC) estimates that roughly one out of six Americans or 48 million people is sickened by food borne illnesses each year. Another 128,000 are hospitalized and approximately 3,000 die of food borne disease every year. In 2011, the CDC (http://www.cdc.gov/outbreaknet/foodborne-surveillance-questions-and-answers.html) estimated that salmonellosis resulted in 20,000 hospitalizations and 378 cases of death per year. It has also estimated that *Escherichia coli* O157:O7 causes approximately 62,000 cases of food borne disease and approximately 1,800 food borne illness-related hospitalizations in the United States annually. A study by the Pew Charitable Trusts of Georgetown University suggested that food borne illnesses cost the United States $152 billion in health-related expenses each year (Yeager, 2010).

A study commissioned by the UK Food Standard Agency (FSA) found that campylobacter was one of the main causes of Infectious Intestinal Diseases (IID) and was responsible for around 500,000 cases annually. The same agency also reported that two thirds of chicken samples on sale within the UK were contaminated with campylobacter (http://www.food.gov.uk/policy-advice/microbiologykampylobacter-evidenceprogramme/campybackground).

The world's tendency to find more natural and/or organic antimicrobials has resulted in a great amount of research in identifying these type of products as well as an increased cost of new raw materials due to low commercial availability of natural/organic products. Currently many type of chemicals and their combinations are used as antimicrobials. These chemicals include organic acids, aldehydes, ester of organic acids, plant extracts and others.

One of the components of the present invention are organic acid esters. Several US patents and WO patents described the use of organic acid esters as flavorings, preservatives or antimicrobials. U.S. Pat. No. 7,652,067 and WO Patent #2009/037270 suggest of the use of a hydrophobic organic compound i.e. menthol, with a monoester of a saturated organic acid of $C_6$-$C_{20}$ carbon length. This product is useful for flavoring food and perfumery. These patents do not suggest of a combination of organic acid esters combined with organic acids and aldehydes as antimicrobials. US Patent Application #2009/0082253, suggests of an antimicrobial comprising a mixture of organic acid esters of lactic acid (lactylate), a hydroxyl carboxylic acid and an antibacterial agent. They do not suggest that the mixture of esters of organic acids other than lactic acids ester and polylysine, a known antimicrobial, will result in an effective antimicrobial. U.S. Pat. No. 7,862,842 suggest the use of organic acid ethyl esters derived from lauric acid and arginine preservative for perishable food product not as animal feed preservative.

The present invention suggests the use of organic acid esters in combination with aldehydes and organic acids as an antimicrobial in feed ingredients, feed and water. Literature review has shown that organic acid esters have been studied as bactericides and fungicides against plant and human pathogens. Propyl, methyl and ethyl esters of ferulic acid were effective in inhibiting *Saccharomyces cerevisiae, Aspergillus fumigatus* and *Aspergillus flavus* (Beck, et. al, 2007). Organic acids esters prepared from mixing n-organic alcohols and dibasic acids were used as plasticizer and exhibited some benefits as a fungicide (Sadek, et. al., 1994). Six organic acid esters from soybean, including methyl and ethyl palmitates, methyl and ethyl oleates, methyl linoleate and methyl linolenate demonstrated curative and protective activities against powdery mildew in barley. Methyl laurate has also been reported to control the development of powdery mildew (Choi, et. al., 2010). Castor oil methyl ester can replace mineral oil to control the fungal disease, Black Sigatoka, in bananas (Madriz-Guzman, et. al., 2008). Organic acid methyl esters from linoleic, linolenic, arachidonic, palmitoleic and oleic acids were effective in inhibiting growth of *Streptococcus mutans, Candida albicans, Aggregatibacter actinomycetemcomitans, Fusobacterium nucleatum* and *Porphyromonas gingivalis* (Huang, et. al., 2010). The fungus *Muscodor albus* produces certain volatiles compounds that effectively inhibit and kill other fungi and bacteria. One of these volatile compounds is an ester of 1-butanol, 3-methyl acetate, which is 62% of the total esters that was effective in inhibit growth of several fungi (Strobel, et. al., 2001). The organic acid methyl ester profile from *Sesuvium portulacastrum* indicates the presence of palmitic, oleic, linoleic, linolenic, myristic and beheni acid esters, all of them effective against several human pathogenic microorganisms (Chandrasekaran, et. al., 2011). Organic acid methyl esters of dodecanoic and pentadecanoic acids found in carrots extract were effective against *Leuconostoc mesenteroides, Listeria monocytogenes, Staphylococcus aureus, Pseudomonas fluorescens, Candida albicans* and *E. coli* (Babic, et. al., 1994). The inhibitory activity against *E. coli, L. monocytogenes, Fusarium culmorum, Bacillus cereus* and *Saccharomyces cerevisiae* was higher when using phenolic acid butyl esters than methyl esters (Merkl, et. al., 2010).

Another compound of the present invention is an aldehyde. One of the most effective of these aldehydes, formaldehyde, has been used as an antiseptic for many years. Two U.S. Pat. Nos. 5,547,987 and 5,591,467 suggest the use of formaldehyde to control *Salmonella* spp. in animal feed. These patents do not suggest that the combination of formaldehyde or other aldehydes with organic acid esters provides a synergistic effect as described in the present invention.

An aldehyde used in the present invention is trans-2-hexenal, a six carbon, double bond aldehyde, $C_6H_{10}O$ and MW=98.14. Trans-2-hexenal is present in many edible plants such as apples, pears, grapes, strawberries, kiwi, tomatoes, olives, etc. The use of plants and plant extracts have been successful in identifying new anti-microbials. For example, the extract from cashew apple was observed to effective against *Helicobacter pylori* and *S. cholerasuis* at concentrations of 50-100 ug/ml. The two main components were found to be anacardic acid and trans-2-hexenal. The minimum inhibitory and minimum biocidal activity of trans-2-hexenal were determined to be 400 and 800 ug/ml, respectively (Kubo, et. al., 1999; Kubo and Fujita, 2001). Kim and Shin (2004) found that trans-2-hexenal (247 mg/L) was effective against *B. cereus, S. typhimurium, V. parahaemolyticus, L. monocytogenes, S. aureus* and *E. coli* O157:H7. Nakamura and Hatanaka (2002) demonstrated that trans-3-hexenal was effective in controlling *Staphylococcus aureus, E. coli* and *Salmonella typhimurium* at a level of 3-30 ug/ml. Trans-2-hexenal completely inhibited proliferation of both *P. syringae* pathovars (570 µg/L of air) and *E. coli* (930 micrograms/L of air)(Deng, et. al., 1993). It was observed that trans-2-hexenal at 250 ug/ml was effective on inhibiting the growth of *Phoma mycelium* (Saniewska and Saniewski, 2007). In a study to control mold in fruits, it was found that trans-2-hexenal was not phytotoxic to apricots, but it was phytotoxic for peaches and nectarines at 40 µl/l (Neri, et. al., 2007). Trans-2-hexenal (12.5 µl/l) was effective on controlling *Penicillium expansum* that causes blue mold (Neri, et. al., 2006a and 2006b). Fallik et. al. (1998) and Hamilton-Kemp et. al. (1991), suggested that trans-2-hexenal vapors inhibited the germination of *Botrytis* spores and apple pollen.

USPTO Application #2007/0087094 suggests the use of at least two microbiocidally active GRAS compounds in combination with less than 50% alcohol (isopropanol or isopropanol/ethanol) as a microbicide. Trans-2-hexenal could be considered one of the GRAS compounds (USPTO Application No. 2007/0087094). Archbold, et. al. (1994) observed that the use of trans-2-hexenal at 0.86 or 1.71 mmol (100 or 200 microliters neat compound per 1.1 L container, respectively) for 2 weeks as for postharvest fumigation of seedless table showed promise for control of mold.

U.S. Pat. No. 5,698,599 suggests a method to inhibit mycotoxin production in a foodstuff by treating with trans-2-hexenal. Trans-2-hexenal completely inhibited the growth of *A. flavus, P. notatum, A. alternate, F. oxysporum, Cladosporium* spp., *B. subtilis* and *A. tumerfaciens* at a concentration of 8 ng/l air. When comparing trans-2-hexenal to citral for the control of yeast ($10^5$ CFU/bottle) in beverages it was found that 25 ppm of trans-2-hexenal and thermal treatment (56° C. for 20 min) was equivalent to 100-120 ppm citral. In beverages that were not thermally treated, 35 ppm of trans-2-hexenal was necessary to control microorganisms (Belleti, et. al., 2007). Trans-2-hexenal has also been reported to control insects, such as *Tibolium castaneum, Rhyzopertha dominica, Sitophilus granaries, Sitophilus orazyzae* and *Cryptolestes perrugineus* (Hubert, et. al., 2008). U.S. Pat. No. 6,201,026 suggests of an organic aldehyde of 3 or more carbons for the control of aphides.

Several patents suggest the use of trans-2-hexenal as a fragrance or perfume. U.S. Pat. No. 6,596,681 suggests the use of trans-2-hexenal as a fragrance in a wipe for surface cleaning. U.S. Pat. No. 6,387,866, U.S. Pat. No. 6,960,350 and U.S. Pat. No. 7,638,114 suggest the use of essential oil or terpenes (e.g. trans-2-hexenal) as perfume for antimicrobial products. U.S. Pat. No. 6,479,044 demonstrates an antibacterial solution comprising an anionic surfactant, a polycationic antibacterial and water, where an essential oil is added as perfume. This perfume could be a terpene such as trans-2-hexenal or other type of terpenes. U.S. Pat. No. 6,323,171, U.S. Pat. No. 6,121,224 and U.S. Pat. No. 5,911,915 demonstrate an antimicrobial purpose microemulsion containing a cationic surfactant where an essential oil is added as a perfume. This perfume can be various terpenes including i.e. trans-2-hexenal. U.S. Pat. No. 6,960,350 demonstrates an antifungal fragrance where a synergistic effect was found when different terpenes were used in combinations (for example trans-2-hexenal with benzaldehyde).

The mode of action of trans-2-hexenal is thought to be the alteration of the cell membrane due to the reaction of hexenal to the sulfhydryl moiety or cysteine residues or formation of Schiff bases with amino groups of peptides and proteins (Deng, et. al., 1993). Trans-2-hexenal is reported to act as a surfactant, but likely permeates by passive diffusion across the plasma membrane. Once inside cells, its α,β-unsaturated aldehyde moiety reacts with biologically important nucleophilic groups. This aldehyde moiety is known to react with sulphydryl groups mainly by 1,4-additions under physiological conditions (Patrignani, et. al., 2008).

Trans-2-hexenal is an inhibitor of phospholipase D, an enzyme that catalyses the hydrolysis of membrane phospholipids that occurs during the maturation and ripening of many types of fruits and vegetables. Therefore, it is suggested that trans-2-hexenal may inhibit ripening (USPTO Application No. 2005/0031744 A1). It is suggested that the inhibition of *Salmonella typhimurium* and *Staphylococcus aureus* by trans-2 hexenal is due to the hydrophobic and hydrogen bonding of its partition in the lipid bilayer. The destruction of electron transport systems and the perturbation of membrane permeability have been suggested as other modes of action (Gardine, et. al., 2001). The inhibition of *P. expansum* decay may be due to damage to fungal membranes of germinating conidia (Neri, et. al., 2006a and 2006b). Studies have been performed to compare trans-2-hexenal to other similar compounds. Deng, et. al. (1993) showed that unsaturated volatiles, trans-2-hexenal and trans-2-hexen-1-ol, exhibited a greater inhibitory effect than the saturated volatiles, hexanal and 1-hexanol. Trans-2-hexenal was more active than hexanal, nonanal and trans-2-octenal against all ATCC bacterial strains (Bisignano, et. al., 2001). Other have found that trans-2-hexenal had lower minimal fungal-growth-inhibiting concentrations than hexanal, 1-hexanol, trans-2-hexen-1-ol, and (Z)-3-hexen-1-ol (basically aldehydes>ketones>alcohols; Andersen, et. al., 1994). Hexenal and hexanoic acid have been reported to be more effective than hexanol in inhibiting *Salmonella* spp. (Patrignani, et. al., 2008).

Muroi, et. al., (1993) suggested that trans-2-hexenal exhibited broad antimicrobial activity but its biological activity (50 to 400 µg/ml) is usually not potent enough to be considered for practical applications. Studies have shown that trans-2-hexenal can potentiate the effectiveness of certain type of antimicrobials. Several patents suggest the use of potentiators for aminoglycoside antibiotics (U.S. Pat. No. 5,663,152), and potentiators for polymyxin antibiotic (U.S. Pat. No. 5,776,919 and U.S. Pat. No. 5,587,358). These potentiators can include indol, anethole, 3-methylindole, 2-hydroxy-6-R-benzoic acid or 2-hexenal. A strong synergic effect was observed when trans-2-eptenal, trans-2-nonenal, trans-2-decenal and (E,E)-2,4-decadienal were tested together (1:1:1:1 ratio) against ATCC and clinically isolated microbial strains (Bisignano et. al., 2001). The prior art has not suggested or observed that the use of trans-2-hexenal in combination with organic acids esters improved the antimicrobial activity of either of the components by themselves Another component of the present invention are organic acids. Commercial mold inhibitors and bactericides are composed of single organic or a mixture of organic acids and/or formaldehyde. The most commonly used acids are propionic, benzoic acid, butyric acid, acetic, and formic acid. The mechanism by which small chain organic acids exert their antimicrobial activity is that undissociated (RCOOH=non ionized) acids are lipid permeable and in this way they can cross the microbial cell wall and dissociate in the more alkaline interior of the microorganism ($RCOOH \rightarrow RCOO^- + H^+$) making the cytoplasm unstable for survival (Van Immerseel, et. al., 2006; Paster, 1979).

Nonanoic acid (nonanoic acid) is a naturally occurring medium chain organic acid. It is oily, colorless fluid, which at lower temperature becomes solid. It has a faint odor compared to butyric acid and is almost insoluble in water. The primary use of nonanoic acid has been as a non-selective herbicide. Scythe (57% nonanoic acid, 3% related organic acids and 40% inert material) is a broad-spectrum post-emergence or burn-down herbicide produced by Mycogen/Dow Chemicals. The herbicidal mode of action of nonanoic acid is due first to membrane leakage during darkness and daylight and second to peroxidation driven by radicals originating during daylight by sensitized chlorophyll displaced from the thylakoid membrane (Lederer, et. al., 2004).

Chadeganipour and Haims (2001) showed that the minimum inhibitory concentration (MIC) of medium chain organic acids to prevent growth of *M. gypseum* was 0.02 mg/ml capric acid and for nonanoic acid 0.04 mg/ml on solid media and 0.075 mg/ml capric acid and 0.05 mg/ml nonanoic in liquid media. These acids were tested independently and not as a mixture. Hirazawa, et. al. (2001) reported that nonanoic acid as well as $C_6$ to $C_{10}$ organic acids were effective in controlling the growth of the parasite, *C. irritans*, and that $C_8$, $C_9$ and $C_{19}$ organic acids were more potent. It was found that *Trichoderma harzianum*, a biocontrol for cacao plants, produces nonanoic acid as one of many chemicals, which was effective in controlling the germination and growth of cacao pathogens (Aneja, et. al., 2005).

Several US patents disclose the use of nonanoic acids as fungicides and bactericides: US Patent Application #2004/026685) discloses a fungicide for agricultural uses that is composed of one or more fatty acids and one or more organic acids different from the fatty acid. In the mixture of the organic acids and the fatty acids, the organic acid acts as a potent synergist for the fatty acid to function as a fungicide. U.S. Pat. No. 5,366,995 discloses a method to eradicate fungal and bacterial infections in plants and to enhance the activity of fungicides and bactericides in plants through the use of fatty acids and their derivatives. This formulation consists of 80% nonanoic acid or its salts for the control of fungi on plants. The fatty acids used are primarily $C_9$ to $C_{18}$. U.S. Pat. No. 5,342,630 discloses a novel pesticide for plant use containing an inorganic salt that enhance the efficacy of $C_8$ to $C_{22}$ fatty acids. One of the examples shows a powdered product with 2% nonanoic acid, 2% capric acid, 80% talc, 10% sodium carbonate and 5% potassium carbonate. U.S. Pat. No. 5,093,124 discloses a fungicide and arthropodice for plants comprising of alpha mono carboxylic acids and their salts. The fungicide consists of the $C_9$ to $C_{10}$ fatty acids, partially neutralized by an active alkali metal such as potassium. The mixture described consists of 40% active ingredient dissolved in water and includes 10% nonanoic, 10% capric acid and 20% coconut fatty acids, all of which are neutralized with potassium hydroxide. U.S. Pat. No. 6,596,763 discloses a method to control skin infection comprised of $C_6$ to $C_{18}$ fatty acids or their derivatives. U.S. Pat. No. 6,103,768 and U.S. Pat. No. 6,136,856 discloses the unique utility of fatty acids and derivatives to eradicate existing fungal and bacterial infections in plants. This method is not preventive but showed effectiveness in already established infections. Sharpshooter, a commercially available product, with 80% nonanoic acid, 2% emulsifier and 18% surfactant, is effective against *Penicillium* and *Botrytis* spp. U.S. Pat. No. 6,638,978 discloses an antimicrobial preservative composed of a glycerol fatty acid ester, a binary mixture of fatty acids ($C_6$ to $C_{18}$) and a second fatty acid ($C_6$ to $C_{18}$) where the second fatty acid is different from the first fatty acid for preservation of food. WO 01/97799 discloses the use of medium chain fatty acids as antimicrobial agents. It shows that an increase of the pH from 6.5 to 7.5 increased the MIC of the short chain ($C_6$ to $C_{18}$) fatty acids.

Nonanoic acid is used as a component of a food contact surface sanitizing solution in food handling establishments. A product from EcoLab consists of 6.49% nonanoic acid as active ingredient to be use as a sanitizer for all food contact surfaces (12CFR178.1010 b). The FDA has cleared nonanoic acid as a synthetic food flavoring agent (21CFR172.515) as an adjuvant, production aid and sanitizer to be used in contact food (12CFR178.1010 b), and in washing or to assist in lye peeling of fruits and vegetables (12CFR173.315). Nonanoic acid is listed by the USDA under the USDA list of Authorized Substances, 1990, section 5.14, Fruit and Vegetable Washing Compounds.

REFERENCES

Andersen, R. A., T. Hamilton-Kemp, D. F. Hilderbrand, C. T. McCraken Jr., R. W. Collins, and P. D. Fleming, 1994. Structure—Antifungal Activity Relationships among Volatile $C_6$ and $C_9$ Aliphatic Aldehydes, Ketones, and Alcohols. J. Agric. Food Chem. 42: 1563-1568.

Aneja, M., T. J. Gianfagna, and K. P. Hebbar, 2005. "*Trichoderma harzianum* produces nonanoic acid, an inhibitor of spore germination and mycelial growth of two cacao pathogens". Physiol. Mol. Plant Pathol. 67: 304-307.

Archbold, D., T. Hamilton-Kemp, A. Clements, and R. Collins, 1994. Fumigating 'Crimson Seedless' Table Grapes with (E)-2-Hexenal Reduces Mold during Long-term Postharvest Storage. HortScience 34(4): 705-707.

Babic, I., S. Aubert, M. J. Amiot and C. Nguyen-The, 1994. Antimicrobial Activity of Shredded Carrot Extracts on Food-borne Bacteria and Yeast. J. Applied Bacteriology 76(2): 135-141.

Beck, J. J., S. C. Chou, B. C. Campbell and J. H. Kim, 2007. Fungicidal Activities of Dihydroferulic Acid Alkyl Ester Analogues. J. Natural Products 70(5): 779-782.

Belletti, N., S. Kamdem, F. Patrignani, R. Lanciotti, A. Covelli, and F. Gardini, 2007. Antimicrobial Activity of Aroma Compounds against *Saccharomyces cerevisiae* and Improvement of Microbiological Stability of Soft Drinks as Assessed by Logistic Regression. AEM. 73 (17): 5580-5586.

Bisignano, G., M. G. Lagana, D. Trombetta, S. Arena, A. Nostro, N. Uccella, G. Mazzanti, and A. Saija, 2001. In vitro antibacterial activity of some aliphatic aldehydes from *Olea europaea* L. *FEMS* Microbiology Letters 198: 9-13.

Chadeganipour and Haims, 2001 Antifungal activities of nonanoic and capric acid on *Microsporum gypseum*. Mycoses 44(3-4): 109-112.

Chandrasekaran, M., A. Senthilkumar and V. Venkatesalu, 2011. Antibacterial and Antifungal Efficacy of Organic Acid Methyl Esters from the Leaves of *Sesuvium portulacastrum* L. Eur. Rev. Med. & Pharmacol. Sci. 15 (7): 775-780.

Choi G. J., K. S. Jang, Y. H. Choi, J. H. Yu, and J. C. Kim, 2010. Antifungal Activity of Lower Alkyl Organic Acid Esters Against Powdery Mildews. The Plant Pathology Journal 26(4): 360.

Deng, W., T. Hamilton-Kemp, M. Nielsen, R. Anderson, G. Collins, and D.; Hilderbrand, 1993. Effects of Six-Carbon Aldehydes and Alcohols on Bacterial Proliferation. J. Agric. Food Chem. 41: 506-510.

Fallik, E., D. D. Archbold, T. R. Hamilton-Kemp, A. M. Cements, R. W. Collins, and M. M. Barth. 1998. (E)-2-hexenal can stimulate *Botrytis cinerea* growth in vitro and on strawberries in vivo during storage. J. Amer. Soc. Hort. Sci. 123:875-881.

Gardini, F.; Lanciotti, R.; Guerzoni, M. E., 2001. Effect of trans-2-hexenal on the growth of *Aspergillus flavus* in relation to its concentration, temperature and water activity. Letters in App. Microbiology 33: 50-55.

Hamilton-Kemp T. R., J. H. Loughrin, D. D. Archbold, R. A. Andersen and D. F. Hildebrand, 1991. Inhibition of pollen germination by volatile compounds including 2-hexenal and 3-hexenal. J Agric. Food Chem 39: 952-956.

Hirazawa, N., 2001. Antiparasitic effect of medium-chain organic acids against ciliated *Cryptocaryon irritans* infestation in the red sea bream *Pagrus major*. Aquaculture 198: 219-228.

Huang, C. B., B. George and J. L. Ebersole, 2010. Antimicrobial Activity of n-6, n-7 and n-9 Organic Acids and Their Esters for Oral Microorganisms. Arch. Oral Biology 55(8): 555-560.

Hubert, J., Z. Munzbergova, and A. Santino, 2008. Plant volatile aldehydes as natural insecticides against stored-product beetles. Pest Manag. Sci. 64: 57-64.

Kim, Y. S. and D. H. Shin, D. H., 2004. Volatile Constituents from the Leaves of *Callicarpa japonica* Thunb. and Their Antibacterial Activities. J. Agric. Food Chem. 52: 781-787.

Kubo, J., J. R. Lee, and I. Kubo, 1999. Anti-*Helicobacter pylori* Agents from the Cashew Apple. J. Agric. Food Chem. 47: 533-537.

Kubo, I. and K. Fujita, 2001. Naturally Occurring Anti-*Salmonella* Agents. J. Agric. Food Chem. 49: 5750-5754.

Lederer, B., T. Fujimori, Y. Tsujino, K. Wakabayashi and P. Boger, 2004. Phytotoxic activity of middle-chain organic acids II: peroxidation and membrane effects. Pesticide Biochemistry and Physiology 80: 151-156.

Madriz-Guzman, A., I. Martinez and M. Guzman, 2008. In vitro Effect and in the Field of Methyl Esters oils from Castor, Palm and Soybean on *Mycosphaerella fijiensis*, Causal Agent of Black Sigatoka in Bananas (Musa AAA). Corbana. 34 (61): 11-27 San Jose: Corporacion bananera Nacional.

Merkl, R., I. Hradkova, V. Filip and J. Smidrkal, 2010. Antimicrobial and Antioxidant Properties of Phenolic Acids Alkyl Esters. Czech J. Food Sci. 28(4): 275-279.

Muroi, H., A. Kubo, and I. Kubo, 1993. Antimicrobial Activity of Cashew Apple Flavor Compounds. J. Agric. Food Chem. 41: 1106-1109.

Nakamura, S. and A. Hatanaka, 2002. Green-leaf-derived C6-aroma compounds with potent antibacterial action that act on both gram-negative and gram-positive bacteria. J. Agric. Food Chem. 50(26): 7639-7644.

Neri, F., M. Mari, S. Brigati, and P. Bertolini, 2007. Fungicidal activity of plant volatile compounds for controlling *Monolinia laxa* in stone fruit. Plant Disease 91(1): 30-35.

Neri, F., M. Mari, A. Menniti, S. Brigati, and P. Bertolini, 2006a. Control of *Penicillium expansum* in pears and apples by trans-2-hexenal vapors. Postharvest Biol. and Tech. 41: 101-108.

Neri, F. M. Mari, A. M. Menniti, and S. Brigati, 2006b. Activity of trans-2-hexenal against *Penicillium expansum* in 'Conference' pears. *J. Appl. Microbiol.* 100: 1186-1193.

Paster, N., 1979. A commercial study of the efficiency of propionic acid and acid and calcium propionate as fungistats in poultry feed, Poult. Sci. 58: 572-576.

Patrignani, F., L. Lucci, N. Belletti, F. Gardini, M. E. Guerzoni, and R. Lanciotti, 2008. Effects of sub-lethal concentrations of hexanal and 2-(E)-hexenal on membrane organic acid composition and volatile compounds of *Listeria monocytogenes, Staphylococcus aureus, Salmonella enteritidis* and *Escherichia coli*. International J. Food Micro. 123: 1-8.

Sadek, E. M., A. M. Motawie, A. M. Hassan and E. A. Gad, 1994. Synthesis and Evaluation of Some Organic Esters as Plasticizers and Fungicides. J. Chem. Technology and Biotechnology. 63(2): 160-164.

Saniewska, S. and M. Saniewski, 2007. The effect of trans-2-hexenal and trans-2-nonenal on the mycelium growth of *Phoma narcissi* in vitro, Rocz. AR. Pozn. CCCLXXXIII, *Ogrodn.* 41: 189-193.

Strobel, S. A., E. Dirkse, J. Sears, and C. Markworth, 2001. Volatile Antimicrobial from *Muscodor albus*, a Novel Endophytic fungus. Microbiology 147: 2943-2950.

Van Immerseel, F., J. B. Russell, M. D. Flythe, I. Gantois, L. Timbermont, F. Pasmans, F. Haesebrouck, and R. Ducatelle, 2006. The use of organic acids to combat *Salmonella* in poultry: a mechanistic explanation of the efficacy. Avian Pathology 35(3): 182-188.

Yeager, D., 2010. Food Safety Update—Report Underscores Need for Enhanced Legislation to Protect Americans Today's Dietitian 12(6): 42.

SUMMARY OF THE INVENTION

One object of the invention is to provide a chemical formulation that improves the microbicidal effect of organic acids. The composition can be a solution containing an organic acid, or a mixture of several organic acids, in combination with an aldehyde and an organic/fatty acid ester.

Another object is to provide an antimicrobial composition for extending the shelf-life of water, food/feed or food/feed ingredients, comprising:

5-25 wt. % nonanoic acid, 1-25 wt. % organic acid ester, 1-50 wt. % of a single or mixture of $C_1$-$C_{24}$ aldehydes a mixture of $C_1$-$C_{24}$ organic acids, and water.

Another object is to provide a method to preserve water, food/feed, and food/feed ingredients, comprising:

spray-treating, in-line mixing, in-line spraying or admixing to water, food/feed or food/feed ingredients, an effective amount of a composition comprising:

5-25 wt. % nonanoic acid, 1-25 wt. % organic acid ester, 1-50 wt. % of a single or mixture of $C_1$-$C_{24}$ aldehydes, a mixture of $C_1$-$C_{24}$ organic acids, and water.

DESCRIPTION OF THE PREFERRED EMBODIMENTS

In this specification and in the claims which follow, reference will be made to a number of terms which shall be defined to have the following meanings.

Definitions

A "weight percent" of a component is based on the total volume of the formulation or composition in which the component is included.

An organic acids of the composition can comprise formic, acetic, propionic, butyric, nonanoic, lactic and other $C_2$ to $C_{24}$ organic acid or mono-, di-, or triglycerides containing $C_1$ to $C_{24}$ fatty acids. These fatty acids comprising small chain, medium chain, long chain fatty acids or small chain, medium chain, long chain triglycerides.

A organic acid ester of the composition can comprise, methyl, ethyl, butyl and propyl organic acid esters or mixtures thereof.

By the term "effective amount" of a compound is meant such amount capable of performing the function of the compound or property for which an effective amount is expressed, such as a non-toxic but sufficient amount of the compound to provide the desired antimicrobial benefits. Thus an appropriate effective amount may be determined by one of ordinary skill in the art using only routine experimentation Formulations can vary not only in the concentration of major components i.e. organic acids, but also in the type of aldehydes, organic acid ester and water concentration used. This invention can be modified in several ways by adding or deleting from the formulation one of the organic acids, aldehyde and type of organic acid ester.

By the terms "synergistic effect or synergy" of the composition is meant to the improved preservative and antimicrobial effect when the ingredients are added as a mixture rather than as individual components.

Composition (s)

A composition of the present invention contains an effective amount of organic acids having 1 to 24 carbons, an aldehyde and organic acid ester.

The organic acids of 1 to 24 carbon chain length may be saturated, unsaturated, cyclic or acyclic organic acids.

The effective mixture of the invention comprises 1 to 70% by volume organic acids, The effective mixture of the invention comprises 1 to 70% by volume nonanoic acid.

The effective mixture of the invention comprises 1 to 50% aldehyde.

The effective mixture of the invention comprises 1 to 50% a organic acid ester.

The effective mixture of the invention comprises 0 to 70% by volume water.

The composition can further comprise a organic acid ester.

The composition can further comprise a organic acid methyl ester.

The composition can further comprise a organic acid ethyl ester.

The composition can further comprise a organic acid butyl ester.

The composition can further comprise a organic acid propyl ester.

The aldehydes of the composition comprise trans-2-pentenal, 2,4-hexadienal, 2,6-nonadienal, trans-2-nonenal, trans-2-hexenal, 10-undecenal, 2,4-decadienal, 2,6-dimethyl-5-heptanal, 2,6-dimethyloctanal, 2-decenal, 2-dodecenal, 2-ethylbutyraldehyde, 2-phenylpropionaldehyde, 2-tridecenal, 3-phenylpropionaldehyde, 9-undecenal, butyraldehyde, cinnamaldehyde, cis-4-heptenal, citral, Citronelloxyacetaldehyde, cuminaldehyde, decanal, furfural, heptanal, hexanal, hydroxycitronellal, Isobutyraldehyde, p-ethoxybenzaldehyde, phenylacetaldehyde, propionaldehyde, p-tolylacetaldehyde, pyruvaldehyde, salicylaldehyde, undecenal, valeraldehyde, veratraldehyde, α-amylcinnamaldehyde, α-butylcinnamaldehyde, α-hexylcinnamaldehyde or other similar aldehydes and their respective alcohol forms.

The composition is effective against various fungi present in food/feed and major food/feed ingredients.

The composition is effective against various bacteria present in food/feed and major food/feed ingredients.

The composition is effective against various bacteria and fungi present in water.

The composition is effective against microbes detrimental for the production of alcohol from fermentation of cellulose, starch or sugars.

Methods

The present invention is effective against bacteria and fungi.

The present invention is applied to water.

The present invention is applied to the food/feed ingredients before entering the mixer.

The present invention is applied to the unmixed food/feed ingredients in the mixer.

The present invention is applied during the mixing of the food/feed ingredients.

The present invention is applied by a spray nozzle.

The present invention is applied by a spray nozzle in an in-line application system.

The present invention is applied in liquid form or as a dry product when mixed with a carrier.

The present invention is applied is such a form that provides a uniform and homogeneous distribution of the mixture throughout the mixed ingredients.

One of the objectives of the present invention is to control the level of microorganisms in food/feed ingredients, food/feed and water. Several mixtures of organic acids, organic acid ester and aldehydes resulted in several formulations that showed effectiveness against bacteria in water and food/feed.

Other objective of the present invention is to formulate an antimicrobial with nature identical occurring compounds or safe to use compounds.

All of the chemicals used in the present invention are currently approved for human uses as antimicrobials, perfumery, flavorings and adjuvants enhancers.

There were unexpected results, i.e. synergism and additive effect, when the organic acids, organic acid ester and aldehydes were used in combination.

Throughout this application, various publications are referenced. The disclosures of these publications in their entireties are hereby incorporated by reference into this application in order to more fully describe the state of the art to which this invention pertains.

Example 1

Methyl and ethyl esters of organic acids were added to test tubes at concentrations of 0.01% and 0.05%. Tubes were vortexed for 10 seconds to uniformly mix the solution. A suspension of *Salmonella typhimurium* (ATTC:14028) was added to each test tube to achieve a final concentration of $10^4$ cfu/ml. The solutions were vortexed, incubated at room temperature for 24 hours and plated on XLT-4 agar. Plates were incubated for 48 hours at 37° C. before enumerating colonies. The effectiveness of each ester as percent reduction compared to the control value is shown in Table 1.

TABLE 1

Effect of Organic acid Esters on Reduction (% Reduction) of *Salmonella typhimurium* in vitro

| | 0.01% Dilution | | 0.05% Dilution | |
|---|---|---|---|---|
| Organic acid | Methyl Ester | Ethyl Ester | Methyl Ester | Ethyl Ester |
| Formic acid | 0 | 67 | 5 | 27 |
| Acetic acid | 0 | 0 | 29 | 0 |
| Propionic acid | 9 | 0 | 19 | 40 |
| Butyric acid | 0 | 28 | 28 | 100 |
| Valeric (pentanoic) acid | 10 | 93 | 100 | 100 |
| Caproic (hexanoic) acid | 99 | 100 | 100 | 100 |
| Caprylic (octanoic) acid | 94 | 66 | 94 | 65 |
| Lauric (dodecanoic) acid | 1 | 0 | 0 | 0 |
| Levulinic acid | 0 | 0 | 12 | 8 |
| Malonic acid | 13 | 36 | 9 | 57 |
| Benzoic acid | 34 | 100 | 100 | 100 |
| Capric (decanoic) acid | 8 | 0 | 0 | 0 |
| Myristic (tetradecanoic) acid | 43 | 12 | 49 | 8 |
| Linoleic acid | 14 | 0 | 0 | 0 |
| Isobutyric acid | 3 | ND* | 41 | ND |
| Isovaleric acid | ND | 61 | ND | 100 |
| Isoamyl acetate | 44 | | 100 | |

*ND not determined

Esters of organic acids with chain lengths of $C_4$ to $C_8$ were observed to be effective against *Salmonella* at the concentrations tested. Ethyl esters were generally more effective than methyl esters. The esters of benzoic acid (an aromatic ring acid) and isoamyl acetate (isoamyl ester of acetic acid) were also observed to have bactericidal activity.

Example 2

Eight organic acid esters ($C_4$-$C_8$ organic acid esters and benzoic acid esters) were blended with trans-2-hexenal, nonanoic acid, propionic acid, acetic acid and water as presented in Table 2. A 25% hexanal: organic acid product (Formula 1) and a formic:propionic acid (90:10, F/P) product were included as positive controls. Formulations were added to test tubes at concentrations of 0.01% and 0.005%. Tubes were vortexed for 10 seconds to uniformly mix the solution.

TABLE 2

Percentage of Ingredients in Test Formulas

| Formula | Nonanoic | Formic | Acetic (56%) | Propionic | trans-2-Hexenal | Organic Acid Ester | Water |
|---|---|---|---|---|---|---|---|
| 1 | 5 | 0 | 20 | 50 | 25 | 0 | 0 |
| 2 | 5 | 0 | 20 | 40 | 15 | 5 | 15 |
| 3 | 5 | 0 | 20 | 40 | 15 | 10 | 10 |
| 4 | 5 | 0 | 20 | 40 | 15 | 20 | 0 |
| 5 | 5 | 0 | 20 | 40 | 10 | 5 | 20 |
| 6 | 5 | 0 | 20 | 40 | 10 | 10 | 15 |
| 7 | 5 | 0 | 20 | 40 | 10 | 20 | 5 |
| 8 | 5 | 0 | 20 | 40 | 5 | 5 | 25 |
| 9 | 5 | 0 | 20 | 40 | 5 | 10 | 20 |
| 10 | 5 | 0 | 20 | 40 | 5 | 20 | 10 |
| 11 | 5 | 0 | 20 | 40 | 0 | 5 | 30 |
| 12 | 5 | 0 | 20 | 40 | 0 | 10 | 25 |
| 13 | 5 | 0 | 20 | 40 | 0 | 20 | 15 |
| F/P | 0 | 90 | 0 | 10 | 0 | 0 | 0 |

A suspension of *Salmonella typhimurium* ($10^4$ cfu/ml) was added to test tubes containing the different dilution of each formulation. The solutions were vortexed, incubated at room temperature for 24 hours and plated on XLT-4 agar. Plates were incubated for 48 hours at 37° C. before enumerating colonies.

The effectiveness of each formulation as percent reduction compared to the control value is shown in the Tables 3 to 10.

TABLE 3

Effect of Methyl Benzoate Formulations on Reduction of *Salmonella typhimurium* (% Reduction) in vitro

| Formula | 0.005% | 0.01% |
|---|---|---|
| 1 | 64 | 100 |
| 2 | 37 | 95 |
| 3 | 58 | 98 |
| 4 | 59 | 100 |
| 5 | 57 | 93 |
| 6 | 55 | 96 |
| 7 | 34 | 95 |
| 8 | 48 | 76 |
| 9 | 42 | 77 |
| 10 | 40 | 88 |
| 11 | 33 | 4 |
| 12 | 39 | 0 |
| 13 | 24 | 0 |
| F/P | 1 | 90 |

TABLE 4

Effect of Ethyl Benzoate Formulations on Reduction of *Salmonella typhimurium* (% Reduction) in vitro

| Formula | 0.005% | 0.01% |
|---|---|---|
| 1 | 64 | 100 |
| 2 | 86 | 99 |
| 3 | 57 | 100 |
| 4 | 68 | 100 |
| 5 | 55 | 98 |
| 6 | 46 | 98 |
| 7 | 71 | 100 |

TABLE 4-continued

| Effect of Ethyl Benzoate Formulations on Reduction of *Salmonella typhimurium* (% Reduction) in vitro | | |
|---|---|---|
| Formula | 0.005% | 0.01% |
| 8 | 51 | 88 |
| 9 | 66 | 89 |
| 10 | 67 | 99 |
| 11 | 40 | 7 |
| 12 | 44 | 6 |
| 13 | 40 | 50 |
| F/P | 1 | 90 |

TABLE 5

| Effect of Ethyl Butyrate Formulations on Reduction of *Salmonella typhimurium* (% Reduction) in vitro | | |
|---|---|---|
| Formula | 0.005% | 0.01% |
| 1 | 50 | 100 |
| 2 | 39 | 99 |
| 3 | 20 | 99 |
| 4 | 1 | 100 |
| 5 | 0 | 97 |
| 6 | 7 | 97 |
| 7 | 4 | 95 |
| 8 | 0 | 70 |
| 9 | 0 | 73 |
| 10 | 0 | 86 |
| 11 | 0 | 0 |
| 12 | 0 | 0 |
| 13 | 0 | 0 |
| F/P | 0 | 51 |

TABLE 6

| Effect of Methyl Octanoate Formulations on Reduction of *Salmonella typhimurium* (% Reduction) in vitro | | |
|---|---|---|
| Formula | 0.005% | 0.01% |
| 1 | 54 | 100 |
| 2 | 62 | 99 |
| 3 | 31 | 100 |
| 4 | 40 | 100 |
| 5 | 26 | 91 |
| 6 | 41 | 98 |
| 7 | 48 | 100 |
| 8 | 30 | 76 |
| 9 | 42 | 92 |
| 10 | 51 | 100 |
| 11 | 0 | 0 |
| 12 | 19 | 18 |
| 13 | 16 | 89 |
| F/P | 0 | 62 |

TABLE 7

| Effect of Methyl Hexanoate Formulations on Reduction of *Salmonella typhimurium* (% Reduction) in vitro | | |
|---|---|---|
| Formula | 0.005% | 0.01% |
| 1 | 67 | 100 |
| 2 | 44 | 99 |
| 3 | 72 | 100 |
| 4 | 47 | 100 |
| 5 | 45 | 100 |
| 6 | 54 | 91 |
| 7 | 64 | 99 |
| 8 | 49 | 76 |
| 9 | 57 | 81 |

TABLE 7-continued

| Effect of Methyl Hexanoate Formulations on Reduction of *Salmonella typhimurium* (% Reduction) in vitro | | |
|---|---|---|
| Formula | 0.005% | 0.01% |
| 10 | 40 | 86 |
| 11 | 42 | 0 |
| 12 | 30 | 0 |
| 13 | 37 | 0 |
| F/P | 0 | 73 |

TABLE 8

| Effect of Ethyl Hexanoate Formulations on Reduction of *Salmonella typhimurium* (% Reduction) in vitro | | |
|---|---|---|
| Formula | 0.005% | 0.01% |
| 1 | 54 | 99 |
| 2 | 15 | 95 |
| 3 | 41 | 95 |
| 4 | 21 | 05 |
| 5 | 10 | 86 |
| 6 | 20 | 87 |
| 7 | 14 | 97 |
| 8 | 0 | 56 |
| 9 | 9 | 58 |
| 10 | 5 | 88 |
| 11 | 0 | 0 |
| 12 | 0 | 0 |
| 13 | 6 | 0 |
| F/P | 0 | 71 |

TABLE 9

| Effect of Methyl Pentanoate Formulations on Reduction of *Salmonella typhimurium* (% Reduction) in vitro | | |
|---|---|---|
| Formula | 0.005% | 0.01% |
| 1 | 36 | 100 |
| 2 | 24 | 98 |
| 3 | 11 | 97 |
| 4 | 22 | 95 |
| 5 | 9 | 84 |
| 6 | 5 | 84 |
| 7 | 23 | 96 |
| 8 | 8 | 59 |
| 9 | 21 | 57 |
| 10 | 14 | 67 |
| 11 | 8 | 0 |
| 12 | 28 | 0 |
| 13 | 7 | 0 |
| F/P | 0 | 98 |

TABLE 10

| Effect of Ethyl Pentanoate Formulations on Reduction of *Salmonella typhimurium* (% Reduction) in vitro | | |
|---|---|---|
| Formula | % 0.005% | 0.01% |
| 1 | 36 | 100 |
| 2 | 41 | 98 |
| 3 | 28 | 97 |
| 4 | 34 | 99 |
| 5 | 16 | 81 |
| 6 | 42 | 95 |
| 7 | 56 | 90 |
| 8 | 19 | 73 |
| 9 | 32 | 77 |
| 10 | 45 | 74 |
| 11 | 41 | 0 |

TABLE 10-continued

| Effect of Ethyl Pentanoate Formulations on Reduction of *Salmonella typhimurium* (% Reduction) in vitro | | |
|---|---|---|
| Formula | % 0.005% | 0.01% |
| 12 | 52 | 45 |
| 13 | 50 | 5 |
| 14 | 0 | 98 |

Conclusions: The addition of 5-20% of organic acid ester to an organic acid product containing 5-20% trans-2-hexenal improved the effectiveness of the trans-2-hexenal against *Salmonella*..

Example 3

Eighteen formulations were prepared for in vitro studies as presented in Table 11. A 25% trans-2-hexanal: organic acid product (Formula 1) and a formic:propionic acid (90:10, F/P) product were included as positive controls. Formulations were added to test tube at concentrations of 0.005% and 0.01%. Tubes were vortexed for 10 seconds to uniformly mix the solution.

TABLE 11

| Percentage of Ingredients in Test Formulas (%) | | | | | | | | | | |
|---|---|---|---|---|---|---|---|---|---|---|
| Formula | Nonanoic | Formic | Acetic (56%) | Propionic | trans-2-hexenal | Ethyl benzonate | Ethyl hexanoate | Ethyl butyrate | Ethyl pentanoate | Water |
| 1 | 5 | 0 | 20 | 50 | 25 | 0 | 0 | 0 | 0 | 0 |
| 2 | 5 | 0 | 20 | 40 | 5 | 20 | 0 | 0 | 0 | 10 |
| 3 | 5 | 0 | 20 | 40 | 10 | 15 | 0 | 0 | 0 | 10 |
| 4 | 5 | 0 | 20 | 40 | 15 | 10 | 0 | 0 | 0 | 10 |
| 5 | 5 | 0 | 20 | 40 | 20 | 5 | 0 | 0 | 0 | 10 |
| 6 | 5 | 0 | 20 | 40 | 5 | 0 | 20 | 0 | 0 | 10 |
| 7 | 5 | 0 | 20 | 40 | 10 | 0 | 15 | 0 | 0 | 10 |
| 8 | 5 | 0 | 20 | 40 | 15 | 0 | 10 | 0 | 0 | 10 |
| 9 | 5 | 0 | 20 | 40 | 20 | 0 | 5 | 0 | 0 | 10 |
| 10 | 5 | 0 | 20 | 40 | 5 | 0 | 0 | 20 | 0 | 10 |
| 11 | 5 | 0 | 20 | 40 | 10 | 0 | 0 | 15 | 0 | 10 |
| 12 | 5 | 0 | 20 | 40 | 15 | 0 | 0 | 10 | 0 | 10 |
| 13 | 5 | 0 | 20 | 40 | 20 | 0 | 0 | 5 | 0 | 10 |
| 14 | 5 | 0 | 20 | 40 | 5 | 0 | 0 | 0 | 20 | 10 |
| 15 | 5 | 0 | 20 | 40 | 10 | 0 | 0 | 0 | 15 | 10 |
| 16 | 5 | 0 | 20 | 40 | 15 | 0 | 0 | 0 | 10 | 10 |
| 17 | 5 | 0 | 20 | 40 | 20 | 0 | 0 | 0 | 5 | 10 |
| F/P | 0 | 90 | 0 | 10 | 0 | 0 | 0 | 0 | 0 | 0 |

A suspension of *Salmonella typhimurium* ($10^4$ cfu/ml) was added to test tubes containing the different dilution of each formulation. The solutions were vortexed, incubated at room temperature for 24 hours, and plated on XLT-4 agar. Plates were incubated for 48 hours at 37° C. before counting *Salmonella* colonies. The effectiveness of each formulation as percent reduction compared to the control value is shown in Table 12.

TABLE 12

| Effect of Formulations on Reduction of *Salmonella typhimurium* (% Reduction) in Vitro | | |
|---|---|---|
| Formula | 0.005% | 0.01% |
| 1 | 37 | 80 |
| 2 | 10 | 10 |

TABLE 12-continued

| Effect of Formulations on Reduction of *Salmonella typhimurium* (% Reduction) in Vitro | | |
|---|---|---|
| Formula | 0.005% | 0.01% |
| 3 | 1 | 33 |
| 4 | 18 | 68 |
| 5 | 39 | 83 |
| 6 | 0 | 3 |
| 7 | 13 | 36 |
| 8 | 26 | 68 |
| 9 | 37 | 91 |
| 10 | 5 | 0 |
| 11 | 4 | 30 |
| 12 | 25 | 62 |
| 13 | 29 | 85 |
| 14 | 16 | 20 |
| 15 | 10 | 27 |
| 16 | 23 | 60 |
| 17 | 30 | 77 |
| F/P | 27 | 55 |

The addition of 5% of each ester to an organic acid product containing 20% trans-2-hexenal was equivalent in efficacy to the organic acid product containing 25% trans-2-hexenal.

Adding additional ester did not allow for the concentration of trans-2-hexenal to be further decreased.

Example 4

Sixteen formulations were prepared for in vitro studies as presented in Table 13. A formic:propionic acid (90:10, F/P) product was included as positive control. Formulations were added to test tubes at concentration of 0.005% and 0.01%. Tubes were vortexed for 10 seconds to uniformly mix the solution.

TABLE 13

| Percentage of Ingredients in Test Formulas | | | | | | | | | | | | | |
|---|---|---|---|---|---|---|---|---|---|---|---|---|---|
| Formula | Nonanoic | Formic | Acetic (56%) | Propionic | Trans-2-hexanol | Ethyl butyrate | Ethyl benzoate | Methyl benzoate | Ethyl hexa-noate | Methyl octa-noate | Ethyl valerate | Methyl valerate | Water |
| 1 | 5 | 0 | 20 | 50 | 25 | 0 | 0 | 0 | 0 | 0 | 0 | 0 | 0 |
| 2 | 5 | 0 | 20 | 40 | 5 | 5 | 0 | 0 | 0 | 0 | 0 | 0 | 25 |
| 3 | 5 | 0 | 20 | 40 | 5 | 0 | 5 | 0 | 0 | 0 | 0 | 0 | 25 |
| 4 | 5 | 0 | 20 | 40 | 10 | 0 | 0 | 10 | 0 | 0 | 0 | 0 | 15 |
| 5 | 5 | 0 | 20 | 40 | 5 | 0 | 0 | 20 | 0 | 0 | 0 | 0 | 10 |
| 6 | 5 | 0 | 20 | 40 | 5 | 0 | 0 | 0 | 20 | 0 | 0 | 0 | 10 |
| 7 | 5 | 0 | 20 | 40 | 5 | 0 | 0 | 0 | 0 | 10 | 0 | 0 | 20 |
| 8 | 5 | 0 | 20 | 40 | 15 | 0 | 0 | 0 | 0 | 0 | 5 | 0 | 15 |
| 9 | 5 | 0 | 20 | 40 | 15 | 0 | 0 | 0 | 0 | 0 | 10 | 0 | 10 |
| 10 | 5 | 0 | 20 | 40 | 15 | 0 | 0 | 0 | 0 | 0 | 20 | 0 | 0 |
| 11 | 5 | 0 | 20 | 40 | 10 | 0 | 0 | 0 | 0 | 0 | 20 | 0 | 5 |
| 12 | 5 | 0 | 20 | 40 | 15 | 0 | 0 | 0 | 0 | 0 | 0 | 5 | 15 |
| 13 | 5 | 0 | 20 | 40 | 15 | 0 | 0 | 0 | 0 | 0 | 0 | 10 | 10 |
| 14 | 5 | 0 | 20 | 40 | 15 | 0 | 0 | 0 | 0 | 0 | 0 | 20 | 0 |
| 15 | 5 | 0 | 20 | 40 | 10 | 0 | 0 | 0 | 0 | 0 | 0 | 20 | 0 |
| F/P | 0 | 90 | 0 | 10 | 0 | 0 | 0 | 0 | 0 | 0 | 0 | 0 | 0 |

A suspension of *Salmonella typhimurium* ($10^4$ cfu/ml) was added to test tubes containing the different dilution of each formulation. The solutions were vortexed, incubated at room temperature for 24 hours and plated on XLT-4. Plates were incubated for 48 hours at 37° C. before enumerating colonies. The effectiveness of each formulation as percent reduction compared to the control value is shown in Table 14.

TABLE 14

| Effect of Formulations on Reduction of *Salmonella typhimurium* (% Reduction) in vitro | | |
|---|---|---|
| Formula | 0.005% | 0.01% |
| 1 | 73 | 100 |
| 2 | 29 | 78 |
| 3 | 33 | 90 |
| 4 | 39 | 94 |
| 5 | 17 | 84 |
| 6 | 27 | 93 |
| 7 | 44 | 98 |
| 8 | 57 | 100 |
| 9 | 57 | 100 |
| 10 | 45 | 99 |
| 11 | 33 | 97 |
| 12 | 43 | 98 |
| 13 | 37 | 98 |
| 14 | 37 | 95 |
| 15 | 41 | 95 |
| F/P | 0 | 96 |

The addition of organic acid ester to an organic acid product containing 5-15% trans-2-hexenal was equivalent or better in efficacy to the organic acid product.

Example 5

Nine formulations were prepared for in vitro studies as presented in Table 15. Formula 1 was used as a positive control. Formulations were added to test tube at concentration of 0.005% and 0.01%. Tubes were vortexed for 10 seconds to uniformly mix the solution.

TABLE 15

| Percentage of Ingredients in Test Formulas | | | | | | | | | |
|---|---|---|---|---|---|---|---|---|---|
| | Formulas | | | | | | | | |
| Ingredients | 1 | 2 | 3 | 4 | 5 | 6 | 7 | 8 | 9 |
| Nonanoic | 5 | 5 | 5 | 5 | 5 | 5 | 5 | 5 | 5 |
| Acetic (56%) | 20 | 20 | 20 | 20 | 20 | 20 | 20 | 20 | 20 |
| Propionic | 50 | 40 | 40 | 40 | 40 | 40 | 40 | 40 | 10 |
| trans 2-hexenal | 25 | 15 | 15 | 15 | 15 | 15 | 15 | 15 | 15 |
| Methyl octanoate | | 20 | | | | | | | |
| Methyl benzoate | | | 20 | | | | | | |
| Ethyl benzoate | | | | 20 | | | | | |
| Methyl hexanoate | | | | | 20 | | | | |
| Ethyl hexanoate | | | | | | 20 | | | |
| Ethyl butyrate | | | | | | | 20 | | |
| Ethyl pentanoate | | | | | | | | 20 | |
| Methyl pentanoate | | | | | | | | | 20 |

A suspension of *Salmonella typhimurium* ($10^4$ cfu/ml) was added to three test tubes containing the different dilution of each formulation. The solutions were vortexed, incubated at room temperature for 24 hours and plated on XLT-4. Plates were incubated for 48 hours at 37° C. before counting *Salmonella* colonies. The effectiveness of each formulation as percent reduction compared to the control value is shown in Table 16.

TABLE 16

| Effect of Adding Organic Acid Esters in the Formulation on the Reduction of *Salmonella typhimurium* (% Reduction) in vitro | | | |
|---|---|---|---|
| Formula | Organic ester added | 0.005% | 0.01% |
| 1 | None | 59 | 100 |
| 2 | Methyl octanoate | 62 | 100 |
| 3 | Methyl benzoate | 64 | 100 |
| 4 | Ethyl benzoate | 51 | 100 |
| 5 | Methyl hexanoate | 55 | 100 |
| 6 | Ethyl hexanoate | 55 | 100 |
| 7 | Ethyl butyrate | 54 | 100 |
| 8 | Ethyl pentanoate | 46 | 100 |
| 9 | Methyl pentanoate | 46 | 100 |

The addition of 20% methyl or methyl ester to an organic acid product containing 15% trans-2-hexenal was equivalent in efficacy to the organic acid product containing 25% trans-2-hexenal.

Example 6

Six formulations were prepared for in vitro studies as presented in Table 17. A 25% trans-2-hexanal: organic acid product and formic:propionic (90:10) acid product were included as positive controls. Formulations were added to test tube at concentration of 0.01% and 0.005%. Solutions were vortexed for 10 seconds to uniformly mix the solution.

TABLE 17

Percentage of Ingredients in Test Formulas

| Ingredients | Formulas 1 | 2 | 3 | 4 | 5 | 6 |
|---|---|---|---|---|---|---|
| Nonanoic | 5 | 5 | 5 | 5 | 5 | |
| Formic | | | | | | 90 |
| Acetic (56%) | 20 | 20 | 20 | 20 | 20 | |
| Propionic | 50 | 40 | 40 | 40 | 40 | 10 |
| trans 2-hexenal | 25 | 5 | 10 | 15 | 20 | |
| Ethyl pentanoate | | 20 | 20 | 20 | 20 | |

A suspension of *Salmonella typhimurium* ($10^4$ cfu/ml) was added to test tubes containing the different dilution of each formulation. The solutions were vortexed, incubated at room temperature for 24 hours and plated on XLT-4. Plates were incubated for 48 hours at 37° C. before enumerating colonies. The effectiveness of each formulation as percent reduction compared to the control value is shown in Table 18.

TABLE 18

Effect of Formulations on Reduction of *Salmonella typhimurium* (% Reduction) in vitro

| Formula | 0.005% | 0.01% |
|---|---|---|
| 1 | 0 | 50 |
| 2 | 6 | 16 |
| 3 | 12 | 8 |
| 4 | 22 | 16 |
| 5 | 13 | 46 |
| 6 | 7 | 0 |

The addition of 20% ethyl pentanoate to an organic acid product containing 20% trans-2-hexenal was equivalent in efficacy to the organic acid product containing 25% trans-2-hexenal.

Example 7

In this study the effectiveness of several formulations containing organic acids ester against *Salmonella* spp. were tested in feed. A 90% formic: 10% propionic acid (F/P) product was included as positive control. A dry inoculum containing $10^5$ cfu/g of *Salmonella typhimurium* was added to finely ground poultry feed. Contaminated feed was mixed in a lab mixer equipped with a liquid spray system for 5 minutes and then treated with the different formulations at 0, 1, 2, or 4 Kg/MT (Table 19). After treatment, the contents of the mixer were transferred to one-gallon glass jar, capped and allowed to sit overnight at room temperature (23-25° C.). Samples (four 10 g-subsamples/mixer load) were obtained at 24 hours and/or 7 days after treatment. The 10 g subsamples of feed were transferred to bottles containing 90 mL of Butterfields Phosphate. Dilutions were plated in triplicate on XLT-4 agar. Plates were incubated at 37° C. for 48 hours. After incubation, the level of the *S. typhimurium* on the agar plates was enumerated.

TABLE 19

Percentage of Ingredients in Test Formulas

| Ingredient | Ethyl butyrate G | Ethyl benzoate G | Methyl benzoate E | Methyl benzoate I | Ethyl hexanoate I | Methyl hexanoate I | Methyl octanoate H | Ethyl pentanoate A | Ethyl pentanoate F | Methyl pentanoate A | Methyl pentanoate F |
|---|---|---|---|---|---|---|---|---|---|---|---|
| Propionic acid | 40 | 40 | 40 | 40 | 40 | 40 | 40 | 40 | 40 | 40 | 40 |
| Acetic acid (56%) | 20 | 20 | 20 | 20 | 20 | 20 | 20 | 20 | 20 | 20 | 20 |
| Nonanoic acid | 5 | 5 | 5 | 5 | 5 | 5 | 5 | 5 | 5 | 5 | 5 |
| trans-2-hexenal | 5 | 5 | 10 | 5 | 5 | 5 | 5 | 15 | 10 | 15 | 10 |
| Ethyl butyrate | 5 | 0 | 0 | 0 | 0 | 0 | 0 | 0 | 0 | 0 | 0 |
| Ethyl benzoate | 0 | 5 | 0 | 0 | 0 | 0 | 0 | 0 | 0 | 0 | 0 |
| Methyl benzoate | 0 | 0 | 10 | 20 | 0 | 0 | 0 | 0 | 0 | 0 | 0 |
| Ethyl hexanoate | 0 | 0 | 0 | 0 | 20 | 0 | 0 | 0 | 0 | 0 | 0 |
| Methyl hexanoate | 0 | 0 | 0 | 0 | 0 | 20 | 0 | 0 | 0 | 0 | 0 |
| Methyl octanoate | 0 | 0 | 0 | 0 | 0 | 0 | 10 | 0 | 0 | 0 | 0 |
| Ethyl pentanoate | 0 | 0 | 0 | 0 | 0 | 0 | 0 | 5 | 20 | 0 | 0 |
| Methyl pentanoate | 0 | 0 | 0 | 0 | 0 | 0 | 0 | 0 | 0 | 5 | 20 |
| Water | 25 | 25 | 15 | 10 | 10 | 10 | 20 | 15 | 5 | 15 | 5 |
| Total | 100 | 100 | 100 | 100 | 100 | 100 | 100 | 100 | 100 | 100 | 100 |

The effectiveness of each formulation as percent reduction compared to the control value is shown in Tables 20-30.

TABLE 20

Effect of Ethyl Pentanoate Formulation "A" on Reduction of *Salmonella typhimurium* (% Reduction) in Feed

| Ethyl Pentanoate A | 24 hours |
|---|---|
| Ethyl Pentanoate A - 1 kg/MT | 77 |
| Ethyl Pentanoate A - 2 kg/MT | 92 |
| Ethyl Pentanoate A - 4 kg/MT | 100 |
| F/P 1 kg/MT | 0 |
| F/P 2 kg/MT | 59 |
| F/P 4 kg/MT | 83 |

TABLE 21

Effect of Ethyl Pentanoate Formulation "F" on Reduction of *Salmonella typhimurium* (% Reduction) in Feed

| Ethyl Pentanoate F | 24 hours |
|---|---|
| Ethyl Pentanoate F - 1 kg/MT | 77 |
| Ethyl Pentanoate F - 2 kg/MT | 94 |
| Ethyl Pentanoate F - 4 kg/MT | 94 |
| F/P 1 kg/MT | 53 |
| F/P 2 kg/MT | 74 |
| F/P 4 kg/MT | 93 |

TABLE 22

Effect of Ethyl Butyrate Formulation "G" on Reduction of *Salmonella typhimurium* (% Reduction) in Feed

| Ethyl Butyrate G | 24 hours |
|---|---|
| Ethyl Butyrate G - 1 kg/MT | 70 |
| Ethyl Butyrate G - 2 kg/MT | 85 |
| Ethyl Butyrate G - 4 kg/MT | 92 |
| F/P 1 kg/MT | 76 |
| F/P 2 kg/MT | 77 |
| F/P 4 kg/MT | 95 |

TABLE 23

Effect of Methyl Benzoate Formulation "E" on Reduction of *Salmonella typhimurium* (% Reduction) in Feed

| Methyl Benzoate E | 24 hours |
|---|---|
| Methyl Benzoate E - 1 kg/MT | 52 |
| Methyl Benzoate E - 2 kg/MT | 65 |
| Methyl Benzoate E - 4 kg/MT | 80 |
| F/P 1 kg/MT | 32 |
| F/P 2 kg/MT | 65 |
| F/P 4 kg/MT | 89 |

TABLE 24

Effect of Methyl Benzoate Formulation "I" on Reduction of *Salmonella typhimurium* (% Reduction) in Feed

| Methyl Benzoate I | 24 hours |
|---|---|
| Methyl Benzoate I - 1 kg/MT | 70 |
| Methyl Benzoate I - 2 kg/MT | 83 |
| Methyl Benzoate I - 4 kg/MT | 82 |

TABLE 24-continued

Effect of Methyl Benzoate Formulation "I" on Reduction of *Salmonella typhimurium* (% Reduction) in Feed

| Methyl Benzoate I | 24 hours |
|---|---|
| F/P 1 kg/MT | 79 |
| F/P 2 kg/MT | 84 |
| F/P 4 kg/MT | 97 |

TABLE 25

Effect of Ethyl Benzoate Formulation "G" on Reduction of *Salmonella typhimurium* (% Reduction) in Feed

| Ethyl Benzoate G | 24 hours |
|---|---|
| Ethyl Benzoate G - 1 kg/MT | 72 |
| Ethyl Benzoate G - 2 kg/MT | 85 |
| Ethyl Benzoate G - 4 kg/MT | 88 |
| F/P 1 kg/MT | 76 |
| F/P 2 kg/MT | 77 |
| F/P 4 kg/MT | 95 |

TABLE 26

Effect of Methyl Pentanoate Formulation "A" on Reduction of *Salmonella typhimurium* (% Reduction) in Feed

| Methyl Pentanoate A | 24 hours |
|---|---|
| Methyl Pentanoate A - 1 kg/MT | 49 |
| Methyl Pentanoate A - 2 kg/MT | 50 |
| Methyl Pentanoate A - 4 kg/MT | 96 |
| F/P 1 kg/MT | 42 |
| F/P 2 kg/MT | 84 |
| F/P 4 kg/MT | 96 |

TABLE 27

Effect of Methyl Pentanoate Formulation "F" on Reduction of *Salmonella typhimurium* (% Reduction) in Feed

| Methyl Pentanoate F | 24 hours |
|---|---|
| Methyl Pentanoate F - 1 kg/MT | 80 |
| Methyl Pentanoate F - 2 kg/MT | 91 |
| Methyl Pentanoate F - 4 kg/MT | 98 |
| F/P 1 kg/MT | 53 |
| F/P 2 kg/MT | 77 |
| F/P 4 kg/MT | 93 |

TABLE 28

Effect of Ethyl Hexanoate Formulation "I", Methyl Hexanoate Formulation "I" and Methyl Octanoate Formulation "H" on the Reduction of *Salmonella typhimurium* (% Reduction) in Feed

| Ethyl Hexenoate I | 7 days |
|---|---|
| Ethyl Hexenoate I 1 kg/MT | 69 |
| Ethyl Hexenoate I 2 kg/MT | 79 |
| Ethyl Hexenoate I 4 kg/MT | 88 |
| Methyl Hexenoate I 1 kg/MT | 81 |
| Methyl Hexenoate I 2 kg/MT | 88 |
| Methyl Hexenoate I 4 kg/MT | 95 |
| Methyl Octanoate H 1 kg/MT | 73 |
| Methyl Octanoate H 2 kg/MT | 83 |
| Methyl Octanoate H 4 kg/MT | 92 |

TABLE 28-continued

Effect of Ethyl Hexanoate Formulation "I", Methyl Hexanoate Formulation "I" and Methyl Octanoate Formulation "H" on the Reduction of *Salmonella typhimurium* (% Reduction) in Feed

| Ethyl Hexenoate I | 7 days |
|---|---|
| F/P 1 kg/MT | 81 |
| F/P 2 kg/MT | 91 |
| F/P 4 kg/MT | 98 |

Formulas containing ethyl or methyl pentanoate were as effective as the formic:propionic (F/P) based product.

The invention claimed is:

1. An antimicrobial composition for extending the shelf-life of water, food/feed or food/feed ingredients, the antimicrobial composition comprising:

5-25 wt. % nonanoic acid, 5-10 wt. % methyl pentanoate and/or ethyl pentanoate, 15-20 wt. % of trans-2-hexenal, 50-70 wt. % of acetic acid and/or propionic acid, and water.

2. The composition of claim 1, which comprises:

5-15 wt. % nonanoic acid, 5-10 wt. % methyl pentanoate and/or ethyl pentanoate, 15-20 wt. % of trans-2-hexenal, 10-20 wt. % acetic acid, 40-50 wt. % propionic acid, and water.

3. A method to preserve water, food/feed, and food/feed ingredients, said method comprising:

spray-treating, in-line injecting, in-line mixing or admixing to water, food/feed or food/feed ingredients, an effective amount of a composition comprising:

5-25 wt. % nonanoic acid, 5-10 wt. % methyl pentanoate and/or ethyl pentanoate, 15-20 wt. % of trans-2-hexenal, 50-70 wt. % of acetic acid and/or propionic acid, and water.

4. The method of claim 3, wherein said composition comprises:

5-15 wt. % nonanoic acid, 10-20 wt. % acetic acid, 5-10 wt. % methyl pentanoate and/or ethyl pentanoate, 15-20 wt. % of trans-2-hexenal, 40-50 wt. % propionic acid, and water.

* * * * *